(12) United States Patent
Weijand et al.

(10) Patent No.: US 6,488,652 B1
(45) Date of Patent: *Dec. 3, 2002

(54) SAFETY VALVE ASSEMBLY FOR IMPLANTABLE BENEFICAL AGENT INFUSION DEVICE

(75) Inventors: Koen J. Weijand, Rickanje (NL); Markus Haller, Begnins (CH)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/494,530

(22) Filed: Jan. 31, 2000

Related U.S. Application Data

(63) Continuation-in-part of application No. 09/017,195, filed on Feb. 2, 1998.

(51) Int. Cl.$^7$ .............................................. A61M 11/00
(52) U.S. Cl. ................... 604/93.01; 604/131; 604/891.1
(58) Field of Search .................... 604/890.1, 891.1, 604/892.1, 131, 132, 151, 153, 154, 246, 247, 256, 93.01, 65–67, 236, 237, 238

(56) References Cited

U.S. PATENT DOCUMENTS

| | | | |
|---|---|---|---|
| 4,866,326 A | 9/1989 | Niikawa et al. | 310/315 |
| 4,895,500 A | 1/1990 | Hök et al. | 417/566 |
| 5,095,256 A | 3/1992 | Ueyama et al. | 318/116 |
| 5,096,388 A | 3/1992 | Weinberg | 417/322 |
| 5,129,794 A | 7/1992 | Beatty | 417/413 |
| 5,147,141 A | 9/1992 | Sakaida et al. | 400/124 |
| 5,171,132 A | 12/1992 | Miyazaki et al. | 417/413 |
| 5,207,666 A | * 5/1993 | Idriss et al. | 128/DIG. 12 |
| 5,224,843 A | 7/1993 | van Lintel | 417/413 A |
| 5,257,987 A | * 11/1993 | Athayde et al. | 128/DIG. 12 |
| 5,259,737 A | 11/1993 | Kamisuki et al. | 417/322 |
| 5,413,955 A | 5/1995 | Lee et al. | 437/86 |
| 5,479,062 A | 12/1995 | Yoshino | 310/316 |
| 5,607,418 A | * 3/1997 | Arzbaecher | 128/DIG. 12 |
| 5,993,414 A | * 11/1999 | Haller | 604/131 |
| 6,048,328 A | * 4/2000 | Haller et al. | 604/131 |
| 6,203,523 B1 | * 3/2001 | Haller et al. | 604/131 |
| 6,315,769 B1 | * 11/2001 | Peer et al. | 604/132 |

FOREIGN PATENT DOCUMENTS

| | | | |
|---|---|---|---|
| JP | 6397854 A | 4/1988 | F02D/41/20 |
| JP | 2058280 A | 2/1990 | H01L/41/09 |
| JP | 2136245 A | 5/1990 | B41J/2/30 |
| JP | 4309273 A | 10/1992 | H01L/41/09 |
| JP | 4351200 A | 12/1992 | H04R/17/10 |
| JP | 5003683 A | 1/1993 | H02N/2/00 |
| JP | 5344755 A | 12/1993 | H02N/2/00 |
| JP | 6177449 A | 6/1994 | H01L/41/09 |

* cited by examiner

Primary Examiner—Brian L. Casler
Assistant Examiner—Kevin C. Sirmon
(74) Attorney, Agent, or Firm—Thomas F. Woods; Eric R. Waldkoetter; Tom G. Berry

(57) ABSTRACT

An implantable beneficial agent infusion device featuring a unique safety valve assembly is disclosed. In one embodiment of the present invention, a seal in the safety valve assembly is normally closed and only opens upon a deflectable or moveable member to which the seal is attached being electrically, magnetically or electromagnetically activated. The valve assembly is preferably small in size and made of corrosion resistant materials. The valve assembly may be employed in either a passive or an active implantable drug or beneficial agent infusion system.

56 Claims, 8 Drawing Sheets

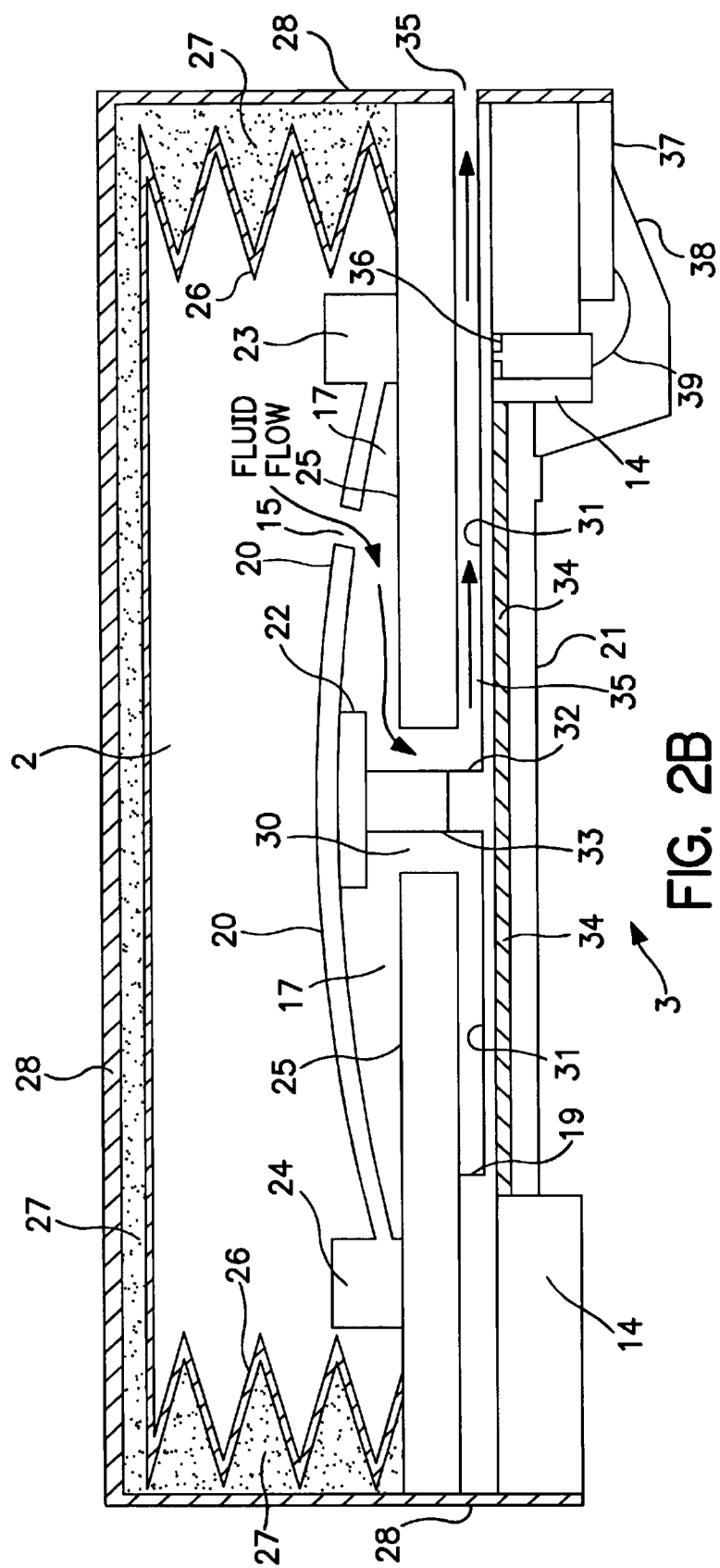

SAFETY VALVE ASSEMBLY FOR IMPLANTABLE BENEFICIAL AGENT INFUSION DEVICE

RELATED APPLICATION

This application is a continuation in part of application Ser. No. 09/017,195, filed Feb. 2, 1998.

This patent application is a continuation-in-part of U.S. patent application Ser. No. 09/017,195 to Haller et al. Entitled "Implantable Drug Infusion Device Having a Safety Valve Assembly", the disclosure of which is hereby incorporated by reference herein in its entirety.

FIELD OF THE INVENTION

The present invention relates to the field of implantable medical devices, and more particularly to a safety valve assembly for an implantable drug infusion device.

BACKGROUND OF THE INVENTION

Implantable drug infusion devices are used to provide patients with a constant and long term dosage or infusion of a drug or any other therapeutic agent. Essentially such device may be categorized as either active or passive.

Active drug or programmable infusion devices feature a pump or a metering system to deliver the drug into the patient's system. An example of such an active drug infusion device currently available is the Medtronic SynchroMed programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed pump further includes an antenna to permit the remote programming of the pump.

Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™. This device delivers the drug into the patient through the force provided by a pressurized reservoir. In particular, this reservoir is pressurized with a drug to between 20–40 psi through a syringe capable of delivering the fluid between 35–55 psi.

Regardless of whether the device is an active or passive drug infusion device, the overriding concern for all drug infusion devices is to ensure patient safety. This includes, among many other things, that only the exact intended amount of drug is delivered to the patient. Thus, one drawback to active devices which feature pumps that are not normally closed, such as those seen in U.S. Pat. Nos. 5,277,556; 5,224,843 and 5,219,278, is that if the device malfunctions or changes occur in the fluid pathway, then more drug than intended may reach the patient. Similar risks are inherent in passive devices which, should the flow regulator fail or the pressure reservoir be over pressurized, may lead to more drug than intended to reach the patient.

Thus there is a need for a drug infusion system which features a safety valve assembly which will provide an additional margin of safety to the patient.

SUMMARY OF THE INVENTION

The present invention is an implantable beneficial agent or drug infusion device, which features a unique safety valve assembly. In one embodiment of the present invention, the safety valve assembly comprises a seal which is normally closed and opens only upon being a deflectable or moveable member to which the seal is attached being electrically, magnetically or electro-magnetically activated. The valve assembly is preferably small in size and made of corrosion resistant materials. The valve assembly may be employed in either a passive or an active drug or beneficial agent implantable infusion system.

BRIEF DESCRIPTION OF THE DRAWINGS

FIG. 2B shows the safety valve assembly of FIG. 2B in an open position, thereby permitting fluid egress from the reservoir thereof.

The Figures are not necessarily to scale.

DETAILED DESCRIPTION OF THE PREFERRED EMBODIMENTS

This patent application hereby incorporates by reference into the specification hereof each of the following patent applications, each in its respective entirety: (1) U.S. patent application Ser. No. 09/239,306 to Haller et al. entitled "System for Locating Implantable Medical Device"; (2) U.S. patent application Ser. No. 09/014,196 to Haller et al. entitled "Implantable Drug Infusion Device Having a Flow Regulator"; and (3) U.S. patent application Ser. No. 09/017, 194 to Haller et al. entitled Implantable Drug Infusion Device Having an Improved Valve".

Figure 1:
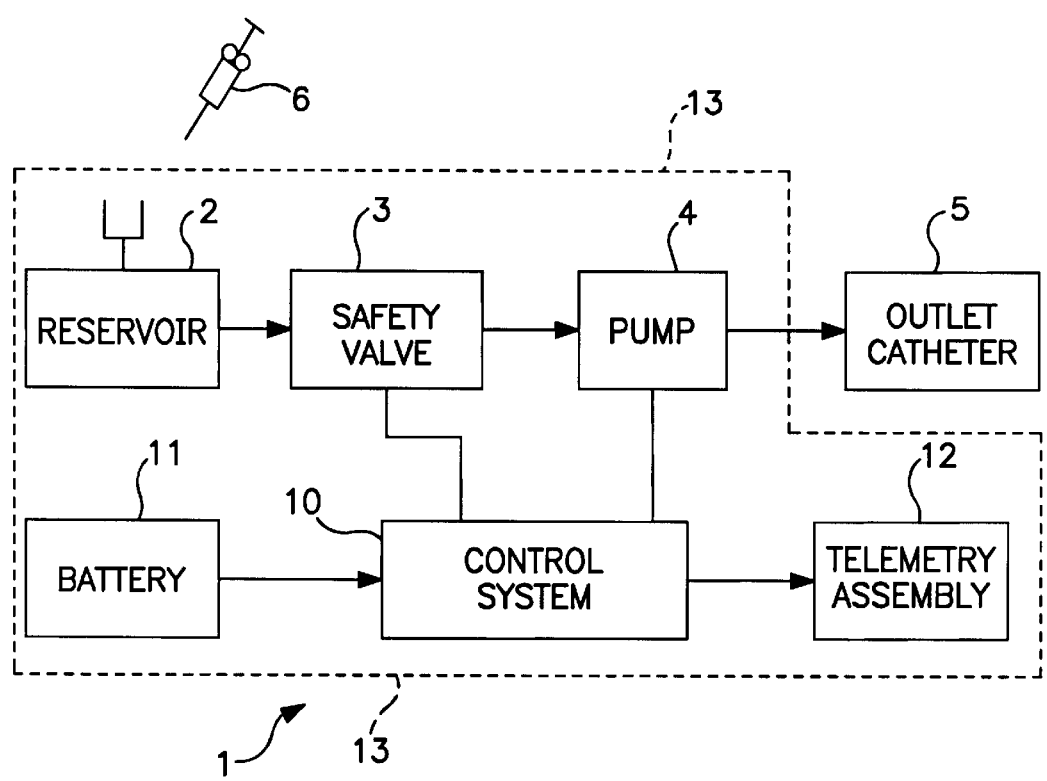
FIG. 1 is a block diagram of the present invention.

FIG. 1 shows a block diagram of the present invention. As seen, such a system 1 comprises a reservoir 2, safety valve assembly 3 assembly, pump 4, electronic controls 10, battery 11, telemetry assembly 12 and outlet catheter 5. Outlet catheter may be of any model desired and suited to the patient's requirements. Safety valve 3 assembly is coupled to the reservoir and also to pump 4. Pump may be of any suitable design, including a roller-type pump as found in the SynchroMed™ or a micro-machined pump, for example. Pump 4 is coupled, in turn to outlet catheter 5, such that fluid form reservoir 2 may be pumped through safety valve assembly and out to outlet catheter. Pump is controlled by electronic controls 10. These controls include, among other devices, an efficient circuit to drive the membranes used in safety valve assembly 3. The device may be refilled through injection port 5 through the use of a needle 6 as is well known. This refill procedure may be further enhanced through the use of the system as described in the above-referenced '306 patent application to Haller. Surrounding all components of the implantable pump other than the outlet catheter is a hermetic closure 13 as is well known in the art. The device may further feature, if desired, a flow regulator, such as that shown in the '196 patent application to Haller.

Figure 2A:
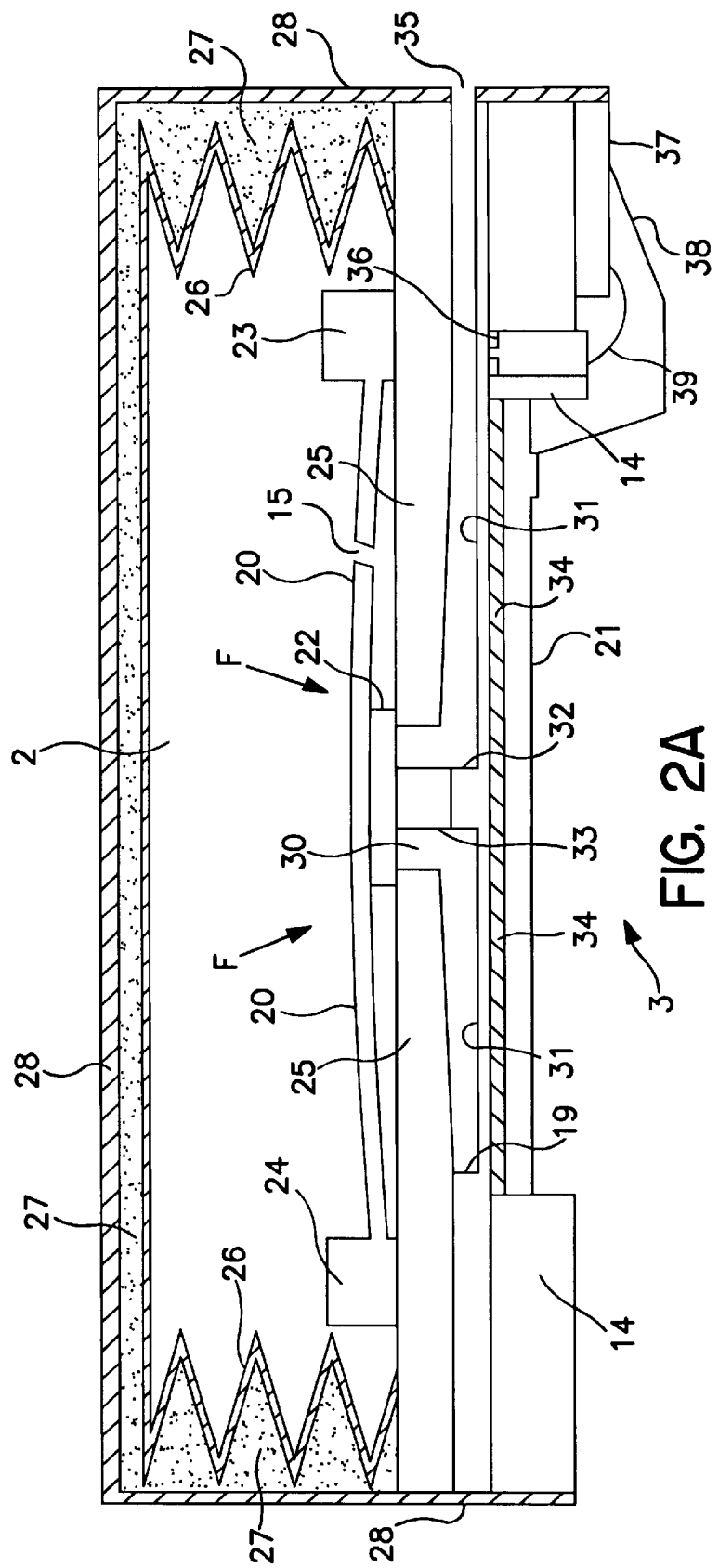
FIG. 2A is a side view of one embodiment of a safety valve assembly of the present invention in a closed position.

FIG. 2A shows a cross-sectional view of one embodiment of safety valve assembly 3 of the present invention in the closed position. Hermetically sealed collapsible reservoir 2 is filled with a desired beneficial agent, drug, medicament, or pharmaceutical such as by needle refilling through a reservoir fill port and self-sealing septum know in the art. Examples of the beneficial agents, drugs, medicaments, and pharmaceuticals that may be infused into a patient's body with the device and method of the present invention include, but are not limited to, gene therapeutic agents, protein- or peptide-based drugs, morphine, BACLOFEN®, antibiotics, and nerve growth factors.

Bellows 26 form the sidewalls of reservoir 2, and are preferably formed from titanium in a manner similar to that employed to form the titanium bellows employed, for example, in the MEDTRONIC® SYNCHROMED® infusion system. Of course, materials other than titanium may be employed to form bellows 26. When formed of titanium, bellows 27 are most preferably about 50 microns to about 75 microns thick.

Propellant 27 is disposed in the volume existing between the outwardly-facing walls of bellows 26 and the inwardly-facing walls of outer walls 28 (within which most of safety valve assembly 3 is disposed). An appropriate formulation of bi-phasic fluorocarbon may be employed as propellant 27, and may be obtained from 3M Corporation in St. Paul, Minn. Propellant 27 is intended to cause a relatively constant pressure to be exerted against the outwardly-facing walls of bellows 26 when held at a temperature at or near human body temperature (e.g., 35–39 degrees Celsius).

Safety valve assembly 3 further includes deflectable upper member or membrane 20, seal 22 mounted on or attached to intermediate member or cap 33/34, first substrate 25, second substrate 14, deflectable or moveable lower member 21, and shoulder 19. Upper membrane 20 is preferably formed of titanium metal and has a thickness ranging between about 25 microns and about 50 microns, but may be thicker (e.g., up to 100 microns) or thinner (e.g., 20 microns). Upper membrane 20 may alternatively be formed of silicone, in which case its thickness would range between about 10 microns and about 20 microns. Upper membrane 20 is preferably 6 to about 15 mm in diameter. Seal 22 most preferably forms an o-ring structure and comprises a deformable material such as silicone rubber, polyimide, TEFLON (PTFE or polytetranfluoroethylene), a polymeric substance, or any other suitable material. Seal 22 preferably has a diameter ranging between 1 and 3 mm, or between about 25 and about 50 microns. Shoulder 19 may be formed of titanium, silicon, or any other suitable material.

Depending on the composition of shoulders 23/24 and first substrate 25, shoulders 23/24 may be attached to substrate 25 by connecting means such as brazing, welding, anodic bonding, or silicon fusion bonding, such means being selected on the basis of the materials forming shoulders 23/24 and first substrate 25. Cap 32/33 is most preferably about 1 mm in height, about one-half the diameter of seal 22 (e.g., between about 0.5 mm and about 1.5 mm), and most preferably comprises nipple 32 formed of silicon, silicone rubber, or titanium or any other suitable material, and end cap 33 formed of glass, silicon, silicone rubber, or titanium or any other suitable material. The height of intermediate member or cap 32/33 is preferably determined by the thicknesses of first substrate 25 and shoulder 19. Cap 32/33 may be glued or otherwise attached to member 31, or alternatively may form a single piece or component in respect of member 31 or lower member 21.

Fluid in reservoir 2 exerts a pressure or force F on the top surface of membrane 20, thereby pushing membrane 20 down, onto and against the upper surface of seal 22. To aid in preventing the undesired opening of safety valve assembly 3, it is preferred that membrane 20, connecting shoulders 23 and 24, seal 22, cap 32/33, and deflectable or moveable lower member 21 be configured and cooperate with one another such that membrane 20 is under mechanical tension and stretched over seal 22, even in the absence of force or pressure provided by fluid disposed in reservoir 2.

The ends of membrane 20 are attached to shoulders 23 and 24 by any of a number of known connecting means such as brazing, welding, anodic bonding, or silicon fusion bonding, such means being selected on the basis of the materials forming upper membrane 20 and shoulders 23 and 24. In the closed position of safety valve assembly 3, the lower surface of seal 22 is pushed down against substrate 25 by upper membrane 20. Cap 32/33 may be formed of two portions, nipple 33 and end cap 34, or may comprise a single portion. The upper surface of cap 32/33 is attached to seal 22, while the lower surface of cap 32/33 is attached to the upper surface of member 31. Connecting member 31, in turn, is preferably attached to deflectable or moveable lower member 21 by electrically conductive epoxy 34 or other suitable means.

The ends of connecting member 31 are attached to substrate 14 by any of a number of known connecting means such as brazing, welding, anodic bonding, or silicon fusion bonding, such means being selected on the basis of the materials forming connecting member 31. Alternatively, connecting member 31 may form a single contiguous piece of material extending laterally away from the edges or perimeter of lower member 21. The upper surface of lower member 21 is preferably attached to connecting member 31 by means of electrically conductive epoxy, the ends of lower member 21 not being attached to second substrate 14. Deflectable or moveable lower member 21 is most preferably formed from a suitable piezo-electric or piezo-crystal material such as PZT (lead zirconium titanate) or PMN (lead magnesium niobate). A piezo-electric material is preferred for deflectable or moveable member 21 because piezo-electric materials are capable of undergoing relatively large displacements when subjected to an electric field. Other embodiments of lower member 21 are contemplated in the present invention, however, such as electrostatic, electro-capacitive and solenoid embodiments of lower member 21, where motion and displacement are imparted to member 21 by means of electric or magnetic fields, or the flow of electrical current.

Integrated circuit 37 is shown as being disposed on the underside of second substrate 14, and preferably receives electrical power from a battery (not shown in FIG. 2A). Integrated circuit 37 comprises a driving circuit, which receives electrical power from a battery or other power source and transforms it into a signal appropriate to cause lower member 21 to move upwardly in response to the application of an electrical filed. It is preferred that integrated circuit 37 provide an output voltage ranging between about +80 and +150 Volts. Wire bonds 38 and 39 provide the electrical connections required to permit such an output voltage to be applied across the top and bottom surfaces of lower member 21. Other electrical connection techniques may be employed than wire bonds to provide the output signal to the lower member including, but not limited to, flextape, solder and the like. Wire bond 39 is most preferably held at ground and electrically connected to electrically conductive epoxy 34 via an electrical connector in feedthrough 36 disposed in second substrate 14. Alternatively, the top end of the electrical connector in feedthrough 36 may be electrically connected to another type of electrically conductive coating or member disposed on the upper surface of deflectable or moveable lower member 21, such as an evaporated, vacuum deposited, electrochemically plated or other electrically conductive plating or member. Wire bond 38 is most preferably switched to a voltage ranging between about +80 and +150 Volts when it is desired to move lower member 21 and seal 22 into the open position.

FIG. 2B shows the safety valve assembly of FIG. 2A in the open position, where deflectable or moveable member 21 has moved upwardly in response to an electrical voltage being applied thereacross by integrated circuit 37. Seal 22, the underside of which is connected to lower member 21 via cap 32/33, member 31 and glue 34, has moved upwardly such that the top surface thereof has engaged and pushed up against the underside of membrane 20 to cause membrane 20 to be deflected upwardly. Fluid present in reservoir 2 and residing in intermediate volume 17 (after having passed through membrane passageway 15) now flows into exit passageway 35 for eventual delivery to the patient. Via catheter and pump means (not shown). Once the voltage applied across lower member 21 is withdrawn, lower member 21 returns to the position illustrated in FIG. 2A and further delivery of the fluid contained in reservoir 2 is terminated.

It is an advantage of the present invention that safety valve assembly 3 is maintained in the closed position when power is withdrawn or lost from the implantable medical device within which it is disposed (e.g., the battery thereof becoming depleted below a certain voltage, etc.), when reservoir 2 is overfilled during refilling, or when external factors such as changes in temperature or pressure occur such that reservoir 2 becomes overpressurized.

The various components of safety valve assembly 3 (e.g., member or membrane 20, seal 22, lower member 21, cap 32/33, etc.) may be configured mechanically such that seal 22 cannot be pushed into the open position, and lower member 21 cannot move upwardly sufficiently to cause seal 22 to open, when a nominal output voltage is applied across lower member 21 and when reservoir 2 has been overfilled to the point of excessive fluid pressures having developed within reservoir 2. That is, the various components of safety valve assembly 3 may be configured such that seal 22 can move into the open position only so long as the pressure or force applied to the upper surface thereof by the fluid contained in reservoir 2 does not exceed a predetermined amount or limit. Such a design prevents the inadvertent and unintended delivery of excessive amounts of the drug contained within reservoir 2 to the patient.

It is contemplated in the present invention that the specific configuration of upper member 20, lower member 21, and seal 22 presented in the drawings hereof be modified such that upper membrane 20 is deflected in response to the provision of an output signal thereto while lower membrane 21 and seal 22 remain in relatively fixed positions.

Figure 3A:
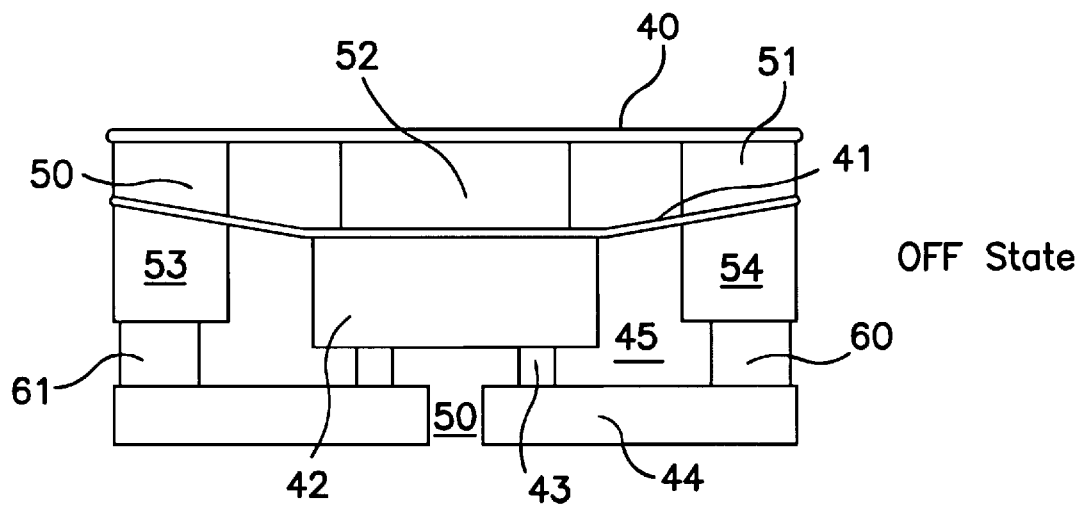
FIGS. 3A and 3B disclose an alternative embodiment of the safety valve assembly of the present invention.
Figure 3B:
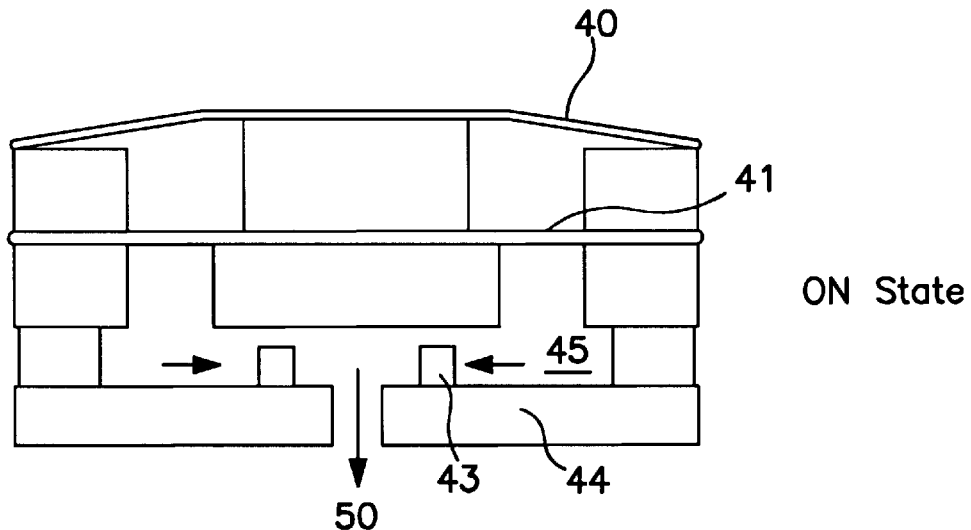

FIGS. 3A and 3B disclose an alternative embodiment of the safety valve assembly of the present invention. Such an embodiment features shape memory alloy membranes as opposed to the piezo-electric membranes disclosed above. This embodiment features a superior membrane 40 and an inferior membrane 41. Membrane 40 is biased in an upward direction while membrane 41 is biased in a downward direction. The respective biasing strengths of these membranes control membrane 40 to normally close the valve when no energy is provided to membrane 41. Upon energizing the membrane 41, however, the shape memory alloy undergoes a reorganization of the crystalline structure. As constructed, this removes the bias to membrane 41. Membrane 40 will, in turn, overcome the bias provided by membrane 41 and thus move the seal assembly 42 upwardly and away from seal footing 43 mounted on substrate 44 thereby creating a fluid passage from cavity 45 to passageway 50. As seen, membrane 40 is mounted across shoulder elements 50 and 51 and includes center portion 52. The shoulder and center portions are preferably constructed of glass. As further seen, membrane 41 is disposed on the downward surface of shoulder and center portion and further mounted to bases 53 and 54. Bases as well as seal assembly 42 are also constructed from glass. This entire assembly is further mounted to substrate 44 through contacts 60 and 61. Contacts 60 and 61 are preferably constructed from silicone. Substrate 44 is preferably constructed of glass while footing 43 is constructed of silicone. Membranes are preferably constructed from Nitinol, although other shape memory alloys may also be used. Moreover, the areas of substrate and membranes in contact with any drug or fluid are further preferably coated with diamond or diamondlike carbon so as to inhibit any interactions between the drug or fluid and the materials. Such coatings may be selected according to the particular drug or fluid to be infused, and may include also tantalum or titanium, for example.

Essentially, the operation of this embodiment may be seen in compared FIGS. 3A and 3B. At rest, or when no energy is provided to membranes, the particular bias to membranes causes seal assembly 42 to snugly engage against footing 43. Once energy is provided to the membranes, the energy or electric current causes the material to heat up and thereby ending the phased transformation, i.e., the crystalline structure is reorganized. Thus seal assembly 42 is caused to disengage against footing 43 and thereby opens a fluid pathway from cavity 45 into passageway 50. Of course, although in this embodiment a double membrane design is shown, other embodiments may feature a single, biased membrane as well as three or more membranes, depending upon the exact fluid pathway required.

One difficulty with all battery powered implantable devices is that they must operate with as little energy drain as possible. A problem typically associated with prior art piezo-electric membranes is that driver circuits typically dissipated the charge built up after a voltage was applied across the membrane. This, of course, wasted energy, and particularly such built-up charge. Another feature of the present invention is the use of a driver circuit which minimizes the energy used. In. particular, the present invention further features a driver circuit which recollects the stored energy on the piezo when the voltage on the piezo is turned to zero.

Figure 4:
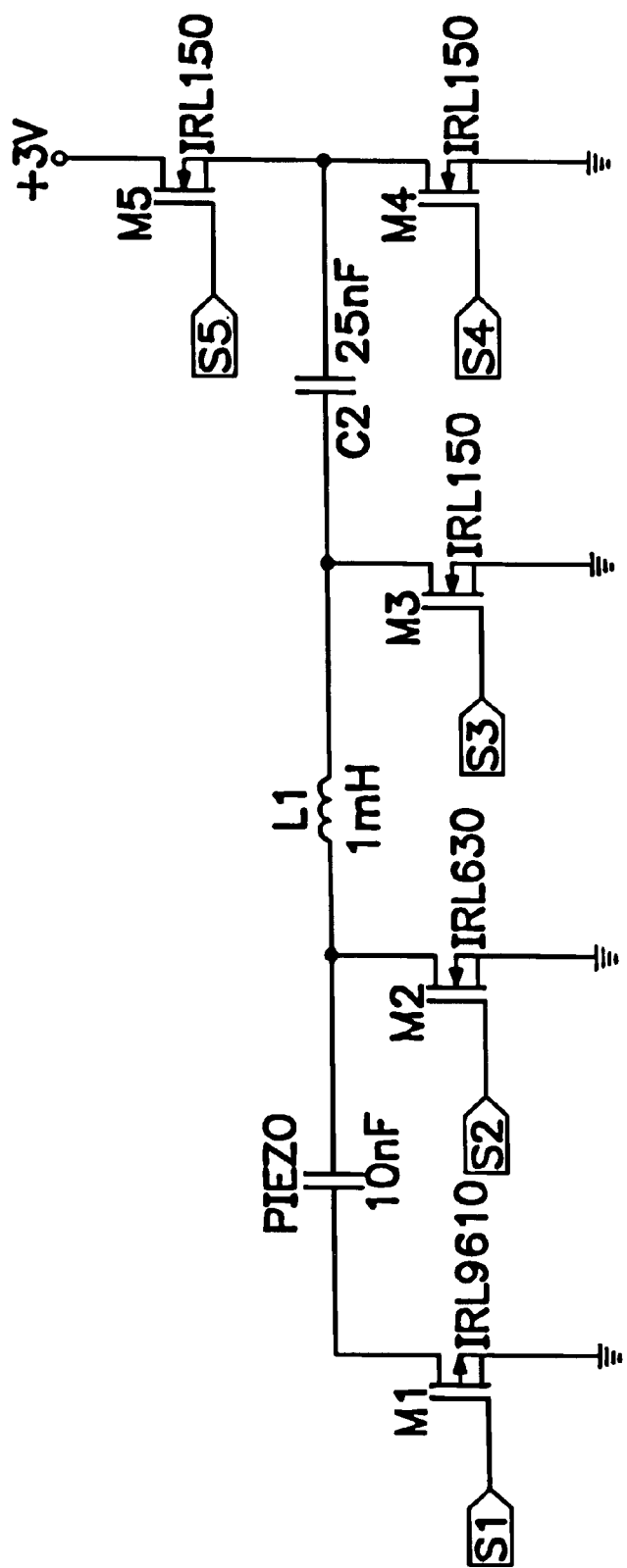
FIG. 4 is a schematic diagram of one embodiment of a driver circuit employed to control a piezo-electric embodiment of the lower member shown in FIGS. 2A and 2B which recollects energy stored on a piezo-electric substrate when the voltage on the piezo-electric member is switched off.
Figure 5:
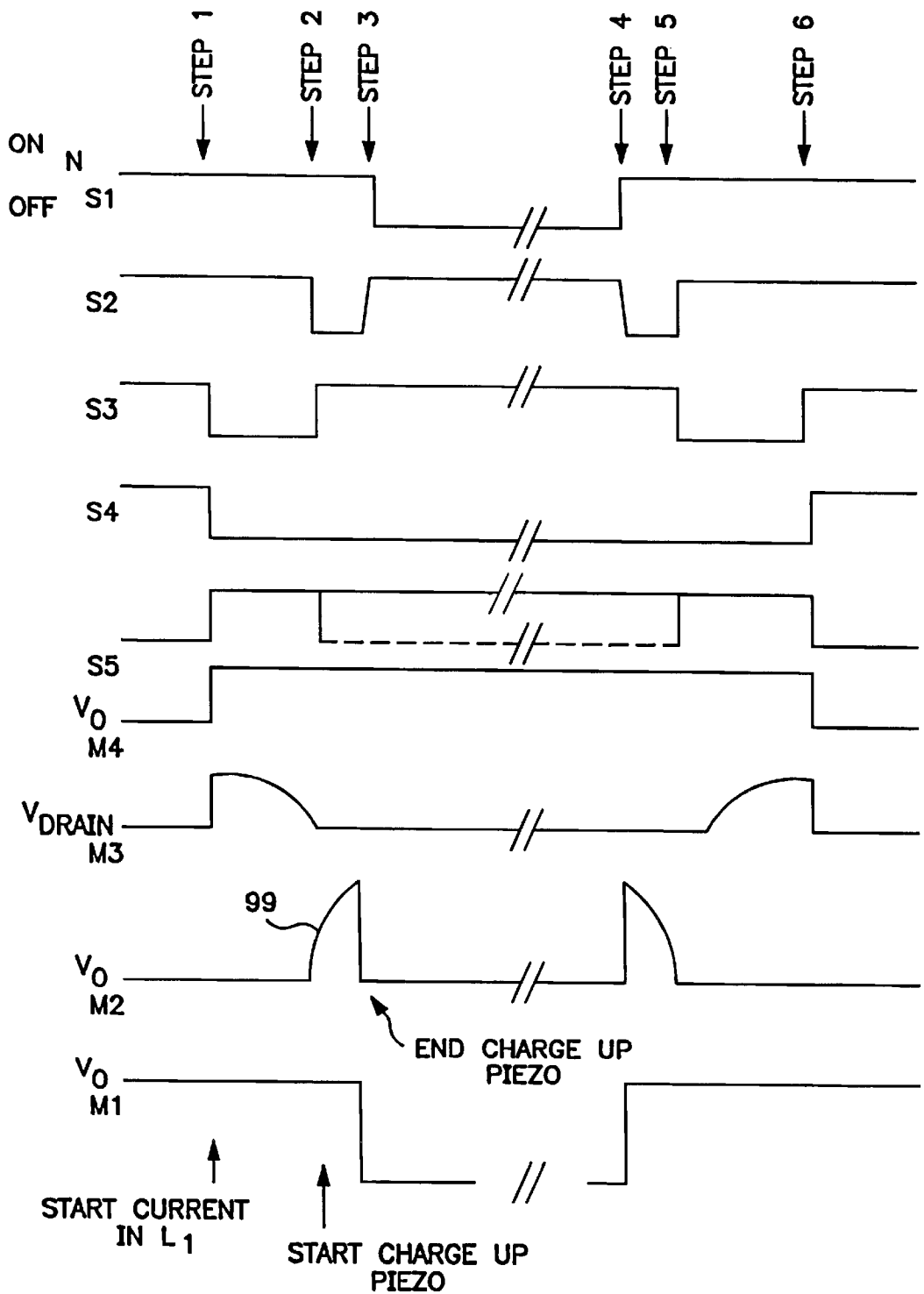
FIG. 5 is a timing diagram of the operation of the driver circuit shown in FIG. 4.

FIG. 4 is a schematic diagram of a driver circuit used to control the piezo membrane of the embodiment shown in FIGS. 2A and 2B which recollects the stored energy on the piezo when the voltage on the piezo is turned to zero. FIG. 5 is a timing diagram of the operation of the driver circuit shown in FIG. 4. Each of these FIGS. will now be described together. As seen, the circuit consists of a 3V power supply, four N-MOS switches with low ohms resistance, 1 P-MOS switch, a storage capacitor and inductor and a piezo membrane. M1 and M2 are high voltage devices while M3–M5 are low voltage devices. At its initial condition, all switches are closed except M5. In step 1 (with reference also to FIG. 5,) M3 and M4 are opened and M5 is closed to thereby charge capacitor C2 through inductor L1. In step 2, M2 is opened and M3 is closed to thereby connecting inductor L1 to piezo. The current in L1 is maintained and a voltage is developed on the drain of M2, as best illustrated by line 99 in FIG. 5, and a voltage is thereby developed across piezo. Once voltage in piezo (or L1) reaches a maximum level step 3 begins. As seen in this step M1 is opened and M2 is closed thereby shorting L1 and maintaining the charge on piezo. Charge actuates the piezo and may be maintained on the piezo for as long as actuation is desired. In steps 4, 5 and 6 the process is reversed. In step 4, M2 is opened, M1 is closed thereby discharging the piezo voltage through the inductor. In step 5 M3 is opened and M2 is closed and the current through L1 is flowed through C2 thereby discharging C2. Finally in step 6, M5 is opened and M3 and M4 are closed, thereby returning to initial conditions. In such a manner the piezo may be driven through a minimal amount of energy. As seen the amount of energy delivered to piezo is determined by the amount of energy delivered to L1, which may be determined by the time which elapses between step 1 and step 2. Of course, if C1 is not completely charged full, then operation is slightly changed, and in step 2 M5 opened, M4 opened and M3 closed. Thereafter the operation remains as described although in step 5 M5 is closed. Additional functionality to monitor voltages or current or both and determine the proper timing for closing the switches is not shown, but would be performed in block 10 of FIG. 1, labeled control system.

Figure 6:
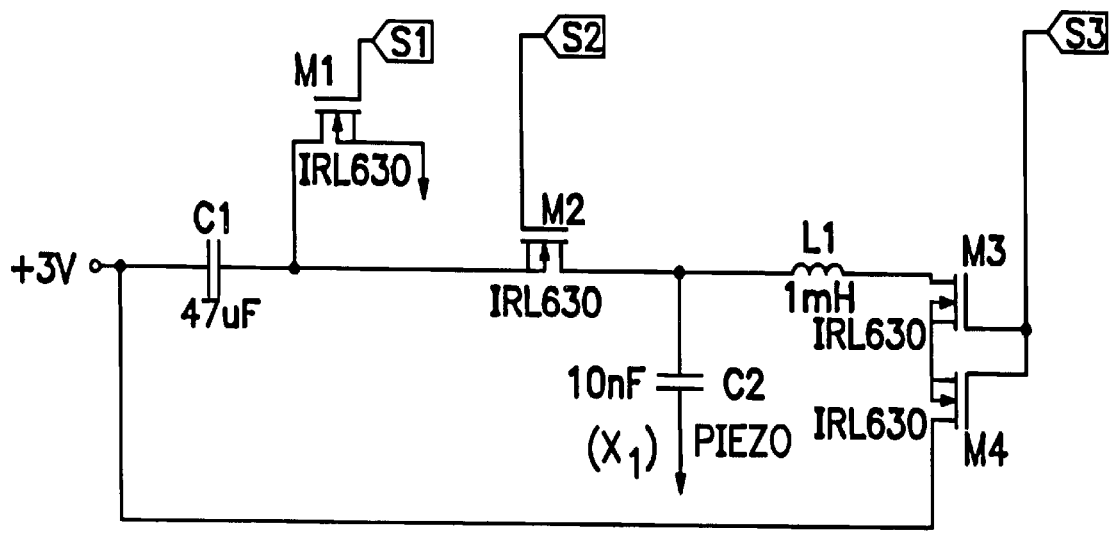
FIG. 6 depicts an alternative driver circuit for a piezo-electric member.
Figure 7:
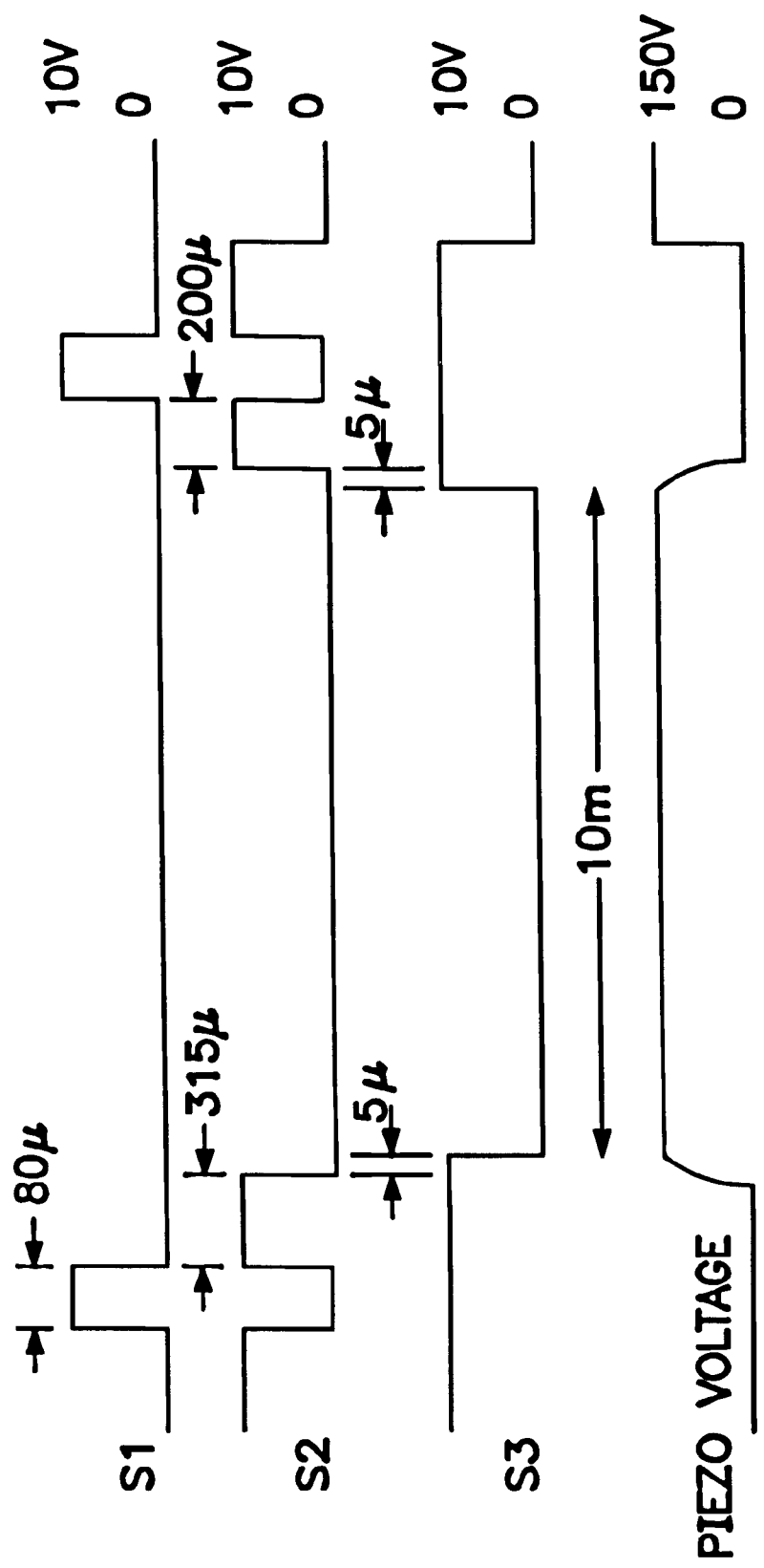
FIG. 7 is a timing diagram of the circuit shown in FIG. 6.

FIG. 6 depicts an alternative driver circuit for the piezo membrane of FIG. 2. FIG. 7 is a timing diagram of the circuit shown in FIG. 6. Each of these FIGS. will now be described together. As seen, this circuit consists of a 3V power supply, a storage capacitor—C1, a piezo model capacitor—C2, an inductor—L1, and four N-MOS switches—M1–M4. The pulses S1–S3 are 10V square wave pulses created by the pulse generation circuit.

The first step in creating the piezo drive pulse is to charge the storage capacitor, C1, to the voltage level of the power supply by closing switches M1 and M3/M4. After C1 is fully charged to the supply voltage, the inductor, L1, is charged with current by discharging the stored energy in C1. This is done by simultaneously opening M1 while closing M2 and keeping M3/M4 closed. Then M2 is reopened while M3/M4 remains closed to charge the piezo, C2, with the stored current. The voltage on C2 rises to 150V and all switches are opened while the pulse remains high.

After the high pulse on the piezo is finished, M3/M4 is closed to drain the energy from the piezo into the inductor L1. After the piezo is drained switch M2 is closed, while M3/M4 remains closed, to charge C2 with the energy stored in the inductor L1. The cycle begins again with another rising edge on M1. The following timing diagram displays the timing sequence for closing of switches M1, M2, and M3/M4 where time units are in seconds.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents and printed publication referenced hereinabove are hereby incorporated by reference herein, each in its respective entirety.

What is claimed is:

1. An implantable beneficial agent infusion device, comprising:

an hermetically sealed enclosure;

a fluid reservoir positioned at least partially within the hermetic enclosure, the fluid reservoir having means for maintaining a fluid containing a beneficial agent disposed therewithin between a first pressure and a second pressure;

means for delivering the fluid into a patient's body;

a controllable pump, the pump communicating with the reservoir and the means for delivering the fluid into a patient's body and causing the fluid to move from the reservoir into the means for delivering a fluid into a patient's body upon receiving a command actuating same; and a safety valve assembly comprising a first substrate, a deflectable, moveable upper member having upper and lower surfaces, a compressible seal having upper and lower surfaces, a deflectable, moveable lower member having upper and lower surfaces, and means for controllably energizing and deflecting the lower member by providing an output signal thereto;

wherein the upper surface of the upper member forms a portion of the fluid reservoir and is in contact with the fluid, the fluid exerting a pressure on the upper surface of the upper member, the lower surface of the upper member engaging the top surface of the seal, the lower surface of the seal being affixed to the lower member and seatable against the first substrate, the upper surface of the seal being seatable against the lower surface of the upper member, the lower surface of the upper member being mechanically biased against the upper surface of the seal when the seal is in a closed position, the energizing and deflecting means being electrically coupled to the upper and lower surfaces of the lower member, the lower member being deflectable or moveable between a first non-energized position in which movement of the fluid from the reservoir into the means for delivering the fluid into the patient's body is blocked and the seal is in a closed position, and a second energized position in which the movement of the fluid from the reservoir into the means for delivering the fluid into the patient's body is permitted as the seal is further pushed against the lower surface of the upper member into an open position through deflection or movement of the lower member occurring in response to the output signal being provided to the lower member, the fluid moving into the means for delivering the fluid into the patient's body and the upper member being deflected further inwardly into the fluid reservoir when the seal is pushed into the open position.

2. The implantable medical device of claim 1, wherein the seal is attached to the lower member by an intermediate member disposed therebetween.

3. The implantable medical device of claim 1, wherein a connecting member is disposed between the seal and the lower member, the connecting member being attached to the upper surface of the lower member.

4. The implantable medical device of claim 1, wherein the upper member is a membrane.

5. The implantable medical device of claim 1, wherein the upper member is formed of a material selected from the group consisting of metal, titanium, and silicone.

6. The implantable medical device of claim 1, wherein the upper member has thickness selected from the group consisting of ranging between about 25 microns and about 100 microns and ranging between about 10 microns and about 20 microns.

7. The implantable medical device of claim 1, wherein the seal comprises a material selected from the group consisting of silicone rubber, PTFE, polyimide and a polymeric substance.

8. The implantable medical device of claim 1, wherein the seal has a diameter ranging between about 1 mm and about 3 mm, or ranging between about 25 microns and about 50 microns.

9. The implantable medical device of claim 1, wherein the seal is attached to the lower member by an intermediate member disposed therebetween, the intermediate member comprising a nipple and an end cap, the end cap being disposed closest to the bottom surface of the seal and the nipple being disposed closest to the lower member.

10. The implantable medical device of claim 9, wherein the nipple comprises a first material selected from the group consisting of glass, silicon, silicone rubber, titanium, and metal and wherein the end cap comprises a second material selected form the group consisting of glass, silicon, silicone rubber, titanium and metal.

11. The implantable medical device of claim 1, wherein the intermediate member has a second diameter which is approximately one-half that of a first diameter of the seal.

12. The implantable medical device of claim 1, wherein the intermediate member has a diameter ranging between about 0.5 mm and about 1.5 mm.

13. The implantable medical device of claim 1, wherein the fluid exerts a pressure against the upper surface of the upper member when the seal is in the open position.

14. The implantable medical device of claim 1, wherein the fluid exerts a pressure against the upper surface of the upper member when the seal is in the closed position.

15. The implantable medical device of claim 1, wherein the upper member further comprises ends, the ends being attached to shoulders.

16. The implantable medical device of claim 1, wherein connecting means attaching the ends of the upper member to the shoulders are selected from the group consisting of brazing, welding, anodic bonding, and silicon fusion bonding.

17. The implantable medical device of claim 1, wherein the lower member comprises a piezo-electric material.

18. The implantable medical device of claim 1, wherein the seal is attached to the lower member by an intermediate member disposed therebetween, a connecting member further being disposed between the intermediate member and the lower member, the connecting member being attached to the upper surface of the lower member.

19. The implantable medical device of claim 1, wherein a connecting member is disposed between the intermediate member and the lower member, the connecting member being attached to the upper surface of the lower member and comprising an adhesive.

20. The implantable medical device of claim 19, wherein the adhesive comprises electrically conductive epoxy.

21. The implantable medical device of claim 1, wherein the lower member comprises an electro-capacitive material.

22. The implantable medical device of claim 1, wherein the lower member comprises an electro-static material.

23. The implantable medical device of claim 1, wherein the lower member comprises a solenoid.

24. The implantable medical device of claim 1, wherein the seal can move into the open position only so long as the pressure of the fluid applied to the upper surface of the upper member does not exceed a predetermined limit.

25. The implantable medical device of claim 1, wherein an integrated circuit comprising a driving circuit receives electrical current from a battery and transforms the current into an output signal appropriate to cause the lower member to move upwardly in response to the application of an electrical field thereto such that the sealing means moves into the open position.

26. The implantable medical device of claim 25, wherein once the output signal applied across the lower member is withdrawn, the seal returns to the closed position.

27. The implantable medical device of claim 1, wherein the safety valve assembly further comprises surfaces which come into contact with the fluid, the surfaces having a coating of diamond or diamond-like carbon disposed thereon to minimize interactions between the fluid and the materials comprising such surfaces.

28. An implantable means for infusing a fluid beneficial agent into a patient's body, comprising:

an hermetically sealed means for enclosing;

a means for containing the fluid positioned at least partially within the enclosing means, the fluid containing means having means for maintaining the fluid disposed therewithin between a first pressure and a second pressure;

means for delivering the fluid into the patient's body;

controllable means for pumping, the pumping means communicating with the fluid containing means and the means for delivering the fluid into a patient's body and causing the fluid to move from the fluid containing means into the means for delivering a fluid into the patient's body upon receiving a command actuating the pumping means; and a safety valve assembly comprising a first substrate, a first upper means for moving having upper and lower surfaces, a means for sealing having upper and lower surfaces, a second lower means for moving having upper and lower surfaces, and means for controllably energizing and deflecting the lower member by providing an output signal thereto or thereacross;

wherein the upper surface of the upper moving means forms a portion of the fluid containing means and is in contact with the fluid, the fluid exerting a pressure on the upper surface of the upper moving means, the lower surface of the upper moving means engaging the top surface of the sealing means, the lower surface of the sealing means being affixed to the lower moving means and seatable against the first substrate, the upper surface of the sealing means being seatable against the lower surface of the upper moving means, the lower surface of the upper moving means being mechanically biased against the upper surface of the sealing means when the sealing means is in a closed position, the energizing and deflecting means being electrically coupled to the upper and lower surfaces of the lower moving means, the lower moving means being deflectable or moveable between a first non-energized position in which movement of the fluid from the reservoir into the means for delivering the fluid into the patient's body is blocked when the sealing means is in a closed position, and a second energized position in which the movement of the fluid from the reservoir into the means for delivering the fluid into the patient's body is permitted as the sealing means is further pushed against the lower surface of the upper moving means into an open position through deflection or movement of the lower moving means occurring in response to the output signal being provided to the lower moving means, the fluid moving into the means for delivering the fluid into the patient's body and the upper moving means being deflected further inwardly into the fluid containing means when the sealing means is pushed into the open position.

29. The implantable medical device of claim 28, wherein the sealing means is attached to the lower moving means by an intermediate member disposed therebetween.

30. The implantable medical device of claim 28, wherein a connecting member is disposed between the sealing means and the lower moving means, the connecting member being attached to the upper surface of the lower moving means.

31. The implantable medical device of claim 28, wherein the upper moving means is a membrane.

32. The implantable medical device of claim 28, wherein the upper moving means is formed of a material selected from the group consisting of metal, titanium, and silicone.

33. The implantable medical device of claim 28, wherein the upper moving means has thickness selected from the group consisting of ranging between about 25 microns and about 100 microns and ranging between about 10 microns and about 20 microns.

34. The implantable medical device of claim 28, wherein the sealing means comprises a material selected from the group consisting of silicone rubber, PTFE, polyimide and a polymeric substance.

35. The implantable medical device of claim 28, wherein the sealing means has a diameter ranging between about 1 mm and about 3 mm, or ranging between about 25 microns and about 50 microns.

36. The implantable medical device of claim 28, wherein the sealing means is attached to the lower moving means by an intermediate member disposed therebetween, the intermediate member comprising a nipple and an end cap, the end cap being disposed closest to the bottom surface of the sealing means and the nipple being disposed closest to the lower moving means.

37. The implantable medical device of claim 27, wherein the nipple comprises a first material selected from the group consisting of glass, silicon, silicone rubber, titanium, and metal and wherein the end cap comprises a second material selected form the group consisting of glass, silicon, silicone rubber, titanium and metal.

38. The implantable medical device of claim 28, wherein the intermediate member has a second diameter which is approximately one-half that of a first diameter of the sealing means.

39. The implantable medical device of claim 28, wherein the intermediate member has a diameter ranging between about 0.5 mm and about 1.5 mm.

40. The implantable medical device of claim 28, wherein the fluid exerts a pressure against the upper surface of the upper moving means when the sealing means is in the open position.

41. The implantable medical device of claim 28, wherein the fluid exerts a pressure against the upper surface of the upper member when the sealing means is in the closed position.

42. The implantable medical device of claim 28, wherein the upper moving means further comprises ends, the ends being attached to shoulders.

43. The implantable medical device of claim 28, wherein connecting means attaching the ends of the upper moving means to the shoulders are selected from the group consisting of brazing, welding, anodic bonding, and silicon fusion bonding.

44. The implantable medical device of claim 28, wherein the lower moving means comprises a piezo-electric material.

45. The implantable medical device of claim 28, wherein the sealing means is attached to the lower moving means by an intermediate member disposed therebetween, a connecting member further being disposed between the intermediate member and the lower member, the connecting member being attached to the upper surface of the lower moving means.

46. The implantable medical device of claim 28, wherein a connecting member is disposed between the intermediate member and the lower moving, the connecting member being attached to the upper surface of the lower moving means and comprising an adhesive.

47. The implantable medical device of claim 46, wherein the adhesive comprises electrically conductive epoxy.

48. The implantable medical device of claim 28, wherein the lower moving means comprises an electro-capacitive material.

49. The implantable medical device of claim 28, wherein the lower moving means comprises an electro-static material.

50. The implantable medical device of claim 28, wherein the lower moving means comprises a solenoid.

51. The implantable medical device of claim 28, wherein the sealing means can move into the open position only so long as the pressure of the fluid applied to the upper surface of the upper moving means does not exceed a predetermined limit.

52. The implantable medical device of claim 28, further comprising means for providing an output signal to the lower moving means, the output signal being suitable to cause the lower moving means to move upwardly in response to the application of an electrical field thereto such that the sealing means moves into the open position.

53. The implantable medical device of claim 52, wherein once the output signal applied across the lower moving means is withdrawn, the sealing means returns to the closed position.

54. The implantable medical device of claim 28, wherein the safety valve assembly further comprises surfaces, the surfaces coming into contact with the fluid having a coating of diamond or diamond-like carbon disposed thereon to minimize interactions between the fluid and the materials comprising such surfaces.

55. A method of making an implantable beneficial agent infusion device, the device comprising an hermetic enclosure, a fluid reservoir positioned at least partially within the hermetic enclosure, the fluid reservoir having means for maintaining a fluid containing a beneficial agent disposed therewithin between a first pressure and a second pressure, means for delivering the fluid into a patient's body, a controllable pump, the pump communicating with the reservoir and the means for delivering the fluid into a patient's body and causing the fluid to move from the reservoir into the means for delivering a fluid into a patient's body upon receiving a command actuating same, and a safety valve assembly comprising a first substrate, a deflectable, moveable upper member having upper and lower surfaces, a compressible seal having upper and lower surfaces, a deflectable, moveable lower member having upper and lower surfaces, and means for controllably energizing and deflecting the lower member by providing an output signal thereto, wherein the upper surface of the upper member forms a portion of the fluid reservoir and is in contact with the fluid, the fluid exerting a pressure on the upper surface of the upper member, the lower surface of the upper member engaging the top surface of the seal, the lower surface of the seal being affixed to the lower member and seatable against the first substrate, the upper surface of the seal being seatable against the lower surface of the upper member, the lower surface of the upper member being mechanically biased against the upper surface of the seal when the seal is in a closed position, the energizing and deflecting means being electrically coupled to the upper and lower surfaces of the lower member, the lower member being deflectable or moveable between a first non-energized position in which movement of the fluid from the reservoir into the means for delivering the fluid into the patient's body is blocked and the seal is in a closed position, and a second energized position in which the movement of the fluid from the reservoir into the means for delivering the fluid into the patient's body is permitted as the seal is further pushed against the lower surface of the upper member into an open position through deflection or movement of the lower member occurring in response to the output signal being provided to the lower member, the fluid moving into the means for delivering the fluid into the patient's body and the upper member being deflected further inwardly into the fluid reservoir when the seal is pushed into the open position, the method comprising:

(a) providing the hermetically sealed enclosure;

(b) providing the fluid reservoir;

(c) providing the means for delivering the fluid into the patient's body;

(d) providing the pump;

(e) providing the safety valve assembly, and (f) operatively connecting the hermetically sealed enclosure, the fluid reservoir, the means for delivering the fluid into the patient's body, the pump and the safety valve assembly to one another.

56. A method of infusing a beneficial agent or drug into a patient with an implantable beneficial agent infusion device, the device comprising an hermetic enclosure, a fluid reservoir positioned at least partially within the hermetic enclosure, the fluid reservoir having means for maintaining a fluid containing a beneficial agent disposed therewithin between a first pressure and a second pressure, means for delivering the fluid into a patient's body, a controllable pump, the pump communicating with the reservoir and the means for delivering the fluid into a patient's body and causing the fluid to move from the reservoir into the means for delivering a fluid into a patient's body upon receiving a command actuating same, and a safety valve assembly comprising a first substrate, a deflectable, moveable upper member having upper and lower surfaces, a compressible seal having upper and lower surfaces, a deflectable, moveable lower member having upper and lower surfaces, and means for controllably energizing and deflecting the lower member by providing an output signal thereto, wherein the upper surface of the upper member forms a portion of the fluid reservoir and is in contact with the fluid, the fluid exerting a pressure on the upper surface of the upper member, the lower surface of the upper member engaging the top surface of the seal, the lower surface of the seal being affixed to the lower member and seatable against the first substrate, the upper surface of the seal being seatable against the lower surface of the upper member, the lower surface of the upper member being mechanically biased against the upper surface of the seal when the seal is in a closed position, the energizing and deflecting means being electrically coupled to the upper and lower surfaces of the lower member, the lower member being deflectable or moveable between a first non-energized position in which movement of the fluid from the reservoir into the means for delivering the fluid into the patient's body is blocked and the seal is in a closed position, and a second energized position in which the movement of the fluid from the reservoir into the means for delivering the fluid into the patient's body is permitted as the seal is further pushed against the lower surface of the upper member into an open position through deflection or movement of the lower member occurring in response to the output signal being provided to the lower member, the fluid moving into the means for delivering the fluid into the patient's body and the upper member being deflected further inwardly into the fluid reservoir when the seal is pushed into the open position, the method comprising:

(a) energizing the lower member and causing same to move;

(b) moving the seal into the open position in response to the lower member being energized and moving, and (c) causing at least a portion of the fluid contained in the reservoir to flow into the means for delivering the fluid into the patient's body.

\* \* \* \* \*